US012768846B2

(12) United States Patent
Lee et al.

(10) Patent No.: US 12,768,846 B2
(45) Date of Patent: Oct. 20, 2026

(54) GOLD NONOCLUSTERS, DOPAMINE BIOSENSORS INCLUDING THEM, AND METHODS FOR DIAGNOSING NEUROLOGICAL DISEASES USING THE SAME

(71) Applicant: Industry-Academic Cooperation Foundation, Yonsei University, Seoul (KR)

(72) Inventors: Dongil Lee, Goyang-si (KR); Hongmei Xu, Seoul (KR); Soomin Ahn, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 711 days.

(21) Appl. No.: 18/194,805

(22) Filed: Apr. 3, 2023

(65) Prior Publication Data

US 2023/0341420 A1 Oct. 26, 2023

(30) Foreign Application Priority Data

Apr. 4, 2022 (KR) ........................ 10-2022-0041733
Oct. 13, 2022 (KR) ........................ 10-2022-0131692

(51) Int. Cl.
*G01N 33/68* (2006.01)
*G01N 33/58* (2006.01)
*G01N 33/94* (2006.01)

(52) U.S. Cl.
CPC ....... *G01N 33/6896* (2013.01); *G01N 33/587* (2013.01); *G01N 33/6848* (2013.01); *G01N 33/9413* (2013.01); *G01N 2800/28* (2013.01)

(58) Field of Classification Search
CPC ................................ B82Y 30/00; C07F 5/025
See application file for complete search history.

(56) References Cited

U.S. PATENT DOCUMENTS 10,775,372 B2 * 9/2020 Mendes ............. G01N 33/5308
2024/0218041 A1 * 7/2024 Weiss .................. C07K 14/622

FOREIGN PATENT DOCUMENTS

| | | | | |
|---|---|---|---|---|
| CN | 108508116 A | 9/2018 | | |
| KR | 10-2019-0103718 A | 9/2019 | | |
| KR | 10-2172084 B1 | 10/2020 | | |
| KR | 102172084 | * 10/2020 | | C07F 1/12 |

OTHER PUBLICATIONS

Wong, Chi-Huey, Bioorganic & Medicinal Chemistry, 22 (2014), pp. 4462-4473.

Alkilany, A. M., et al., "Facile Hydrophobication of Glutathione-Protected Gold Nanoclusters and Encapsulation into Poly(lactide-co-glycolide) Nanocarriers", Scientific Reports, vol. 9, No. 11098, Jul. 31, 2019, pp. 1-11; https://doi.org/10.1038/s41598-019-47543-4.

Zhang, X., et al., "Enhanced Fluorescence of Gold Nanoclusters Composed of HAuCl 4 and Histidine by Glutathione: Glutathione Detection and Selective Cancer Cell Imaging", Small, 2014, 10, No. 24, pp. 5170-5177.

Ahn, S. et al. "A glycopeptide enrichment strategy based on water-soluble gold nanoclusters functionalized with poronic acids"; Department of Chemistry, Yonsei University, Korea; 128th KCS General Meeting and Exhibition E-proceeding, Oct. 13-15, 2021 Program.

Zhong, T., et al. "NIR fluorescence detection of dopamine using 3-aminophyenyl boronic acid-functionalized and lysozyme-templated gold nanoclusters" Anal. Methods, Royal Society of Chemistry; Published May 12, 2017.

Kong, S., et al. "Effective Enrichment Strategy Using Boronic Acid-Functionalized Mesoporous Graphene—Silica Composites for Intact N- and O-Linked Glycopeptide Analysis in Human Serum"; Anal. Chem. 2021, 93, pp. 6682-6691.

Zhang, C., et al. "Hollow MnFe2O4@C@APBA Nanospheres with Size Exclusion and PH Response for Efficient Enrichment of Endogenous Glycopeptides" ACS Appl. Mater. Interfaces 2021, 13, pp. 9714-9728; Downloaded May 15, 2021.

Chen, H., et al. One-step synthesis of boronic acid functionalized gold nanoclusters for photoluminescence sensing of dopamine, Methods Appl. Fluoresc. 5 (2017) 014006; pp. 1-8; Published Mar. 1, 2017; Downloaded Mar. 3, 2017.

Yao, G., et al., "Facile synthesis of 4-mercaptophenylboronic acid functionalized gold nanoparticles for selective enrichment of glycopeptides", Rapid Commun. Mass Spectrom. 2009; 23: 3493-3500; DOI: 10.1002/rcm.4258.

Li, J., et al., "Detecting Proteins Glycosylation by a Homogeneous Reaction System with Zwitterionic Gold Nanoclusters", Anal. Chem. 2017, 89, 4339-4343; DOI: 10.1021/acs.analchem.6b04880.

Tang, J., et al., "On-plate-selective enrichment of glycopeptides using boronic acid-modified gold nanoparticles for direct MALDI-QIT-TOF MS analysis", Proteomics 2009, 9, 5046-5055; DOI 10.1002/pmic.200900033.

(Continued)

*Primary Examiner* — Pancham Bakshi
(74) *Attorney, Agent, or Firm* — DICKINSON WRIGHT PLLC

(57) ABSTRACT

The present invention provides novel gold nanoclusters, a dopamine biosensor including the same that may exhibit reliability in a wide detection range, and a method of quantifying dopamine using the same, and provides a method of diagnosing a neurological disease that exhibits high selectivity for dopamine using the gold nanoclusters. In addition, the present invention provides a method of concentrating glycoproteins that may exhibit improved concentration efficiency and minimize non-specific binding using the gold nanoclusters. A method of analyzing disease-specific glycoproteins which includes the method of concentrating glycoproteins using the gold nanoclusters may be easily used for diagnosis of a disease by identifying different glycoproteins in a patient group compared to a normal group.

5 Claims, 6 Drawing Sheets

(56) References Cited

OTHER PUBLICATIONS

Schumacher, S., et al., "Label-free detection of enhanced saccharide binding at pH 7.4 to nanoparticulate benzoboroxole based receptor units", J. Mol. Recognit. 2011; 24: 953-959; DOI: 10.1002/jmr.1142.

* cited by examiner

σ : Standard deviation of blank sample ($Au_{22}$-BX) signal n : Number of experiments

GOLD NONOCLUSTERS, DOPAMINE BIOSENSORS INCLUDING THEM, AND METHODS FOR DIAGNOSING NEUROLOGICAL DISEASES USING THE SAME

CROSS-REFERENCE TO RELATED APPLICATIONS

This application claims priority under 35 U.S.C. § 119 to Korean Patent Application No. 10-2022-0041733, filed Apr. 4, 2022, and Korean Patent Application No. 10-2022-0131692, filed Oct. 13, 2022, the disclosure of which is incorporated herein by reference in its entirety.

TECHNICAL FIELD

The following disclosure relates to gold nanoclusters, a method of diagnosing a neurological disease using the gold nanoclusters, and a method of concentrating glycoproteins using the gold nanoclusters.

BACKGROUND

Nanoclusters or superatoms, which are composed of a specific number of metal atoms and ligands, follow the macroatomic orbital theory that newly defines valence electrons of particles, which is a theory that considers the nanoclusters or superatoms as one superatom.

Nanoclusters have optical and electrochemical properties that are completely different from nanoparticles because they are more stable than one atom or nanoparticle, and have stronger molecular properties than metallic properties. In particular, as optical, electrical, and catalytic properties of the nanoclusters are sensitively changed according to the number of metal atoms, types of metal atoms, and ligands, studies on the nanoclusters have been actively conducted in a wide variety of fields.

Since these nanoclusters have luminescence properties and are highly likely to be applied in various fields such as light emitting displays, optoelectronic devices, optical sensors, and medical imaging and biodiagnostics, an interest in the nanoclusters has increased. In particular, an interest in biosensors for diagnosing diseases in the biofield is high.

Meanwhile, dopamine, a catecholamine neurotransmitter, is involved in the regulation of various nerve functions such as motor activity, cognition, emotion, mood, reward, addiction, and motivation, and in particular, abnormality of the midbrain dopamine system is a major cause of many mental disorders (diseases) and/or neurological diseases (disorders). For example, it is known that abnormal activity of the midbrain dopamine system has a significant effect on symptoms such as emotional disturbances and addiction diseases, schizophrenia, attention deficit hyperactivity disorder (ADHD), Parkinson's disease, Creutzfeldt-Jakob disease, dementia, Huntington's disease, and psychotropic drug dependence.

Therefore, dopamine analysis is considered a very important means in terms of preventing and treating the neurological diseases described above. In the related art, sensitivity and selectivity of the dopamine analysis are significantly low due to the interference from uric acid, ascorbic acid, and the like. Accordingly, the demand for research and development on an analysis method exhibiting excellent sensitivity and selectivity for dopamine that may solve these problems has increased.

Meanwhile, when human body fluids such as blood and urine are analyzed for diagnosis of a disease, proteins that are expressed differently in abnormal and normal states may be identified, and a method of separating and analyzing these proteins as biomarkers is useful for recognizing pathological conditions of the body, such as tumors, immune responses, and vascular diseases.

Proteins that are expressed differently in the abnormal state are glycosylated or glycated proteins, and glycosylation or glycation of proteins is associated with abnormal actions caused by diseases. Therefore, when these glycoproteins are identified, these glycoproteins may be used as biomarkers for specific diseases, and thus techniques for this have been developed.

However, it is significantly difficult to analyze biomarkers present in trace amounts due to a large number of proteins other than the proteins meaningful as the biomarkers in serum. Therefore, it is significantly important to separate glycoproteins that may be meaningful as biomarkers from serum proteins and concentrate these glycoproteins.

Methods of separating and concentrating glycosylated or glycated proteins according to the related art may be largely divided into a method using liquid chromatography through a hydrophilic interaction or using lectin, a method using a chelating interaction, and a method using hydrazide or boronic acid to form a covalent bond. Such separation and concentration methods according to the related art have problems such as lack of specificity to a sugar, inability to comprehensively concentrate N- and O-glycoproteins, or loss of structural information due to transformation the structure of the sugar or sugar chain during the concentration process. Therefore, there is a need for a method of separating and concentrating glycoproteins by which these problems may be solved.

RELATED ART DOCUMENT

Patent Document (Patent Document 1) Korean Patent Laid-Open Publication No. 10-2011-0031856

(Patent Document 2) Korean Patent Laid-Open Publication No. 10-2020-0081828

(Patent Document 3) Korean Patent Laid-Open Publication No. 10-2012-0125157

(Patent Document 4) Chinese Patent Publication No. 110152624

SUMMARY

An embodiment of the present invention is directed to providing novel gold nanoclusters and a method of preparing the same.

Another embodiment of the present invention is directed to providing a dopamine biosensor including the gold nanoclusters, which may exhibit reliability in a wide detection range, and a method of quantifying dopamine using the gold nanoclusters.

Still another embodiment of the present invention is directed to providing a method of diagnosing a neurological disease which exhibits high selectivity for dopamine using the gold nanoclusters.

Still another embodiment of the present invention is directed to providing a method of concentrating glycoproteins which exhibits improved specificity and excellent concentration efficiency using the gold nanoclusters.

Still another embodiment of the present invention is directed to providing a method of analyzing disease-specific glycoproteins which includes the method of concentrating glycoproteins using the gold nanoclusters.

In one general aspect, there are provided gold nanoclusters represented by the following Chemical Formula 1:

[Chemical Formula 1]

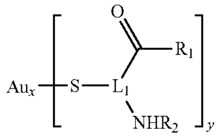

wherein $L_1$ is a trivalent linking group;

the trivalent linking group includes one or two or more linking groups selected from —O—, —C(═O)—, —C(═O)O—, —NH—, and —C(═O)NH—;

$R_1$ is —OH or

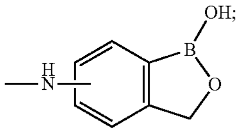

at least one $R_1$ in units y is

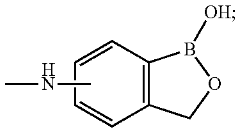

$R_2$ is hydrogen or —C(═O)O—$R_{11}Ar_1$;

at least one $R_2$ in the units y is —C(═O)O—$R_{11}Ar_1$;

$R_{11}$ is C1-C20 alkylene;

$Ar_1$ is C6-C30 aryl;

x is an integer of 10 to 400; and y is an integer of 10 to 100.

$L_1$ may be substituted with one or two or more substituents selected from —OH, —COOH, and —$NH_2$.

$L_1$ may be a trivalent linking group represented by the following Chemical Formula 2 or 3:

[Chemical Formula 2]

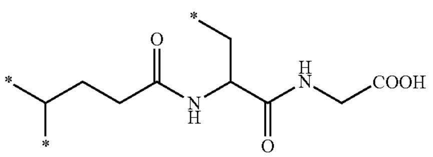

[Chemical Formula 3]

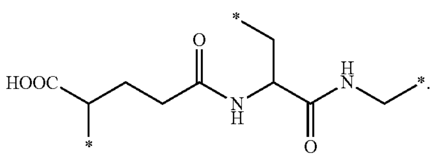

In Chemical Formula 1, $R_{11}$ may be C1-C5 alkylene, $Ar_1$ may be C6-C20 aryl, x may be 18, 22, 25, 38, 67, 102, 144, or 333, and y may be 14, 18, 24, 35, 44, 60, or 79.

In another general aspect, a method of diagnosing a neurological disease includes: separating serum from a collected blood sample; mixing the gold nanoclusters of the present invention with the separated serum to obtain a mixed solution and culturing the mixed solution; measuring fluorescence intensity by irradiating the cultured solution with light; and quantifying dopamine in the blood sample by comparing the fluorescence intensity with a calibration curve.

The neurological disease may be one or two or more selected from a motor disorder, depression, an emotional disturbance, obsessive-compulsive disorder, autism, schizophrenia, attention deficit hyperactivity disorder, Alzheimer's disease, Parkinson's disease, Creutzfeldt-Jakob disease, dementia, and Huntington's disease.

In still another general aspect, a method of concentrating glycoproteins using the gold nanoclusters includes: a) mixing gold nanoclusters represented by the following Chemical Formula 1 with a sample containing glycoproteins; b) separating the gold nanoclusters complexed with the glycoproteins; and c) separating the glycoproteins and the gold nanoclusters:

[Chemical Formula 1]

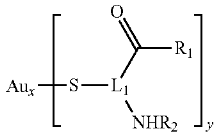

wherein $L_1$ is a trivalent linking group;

the trivalent linking group includes one or two or more linking groups selected from —O—, —C(═O)—, —C(═O)O—, —NH—, and —C(═O)NH—;

each $R_1$ is independently —OH or

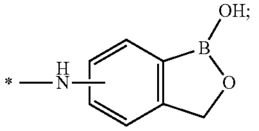

at least one $R_1$ in units y is

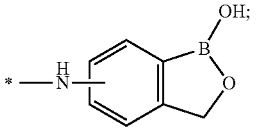

each $R_2$ is independently hydrogen or —C(═O)O—$R_{11}Ar_1$;

at least one $R_2$ in the units y is —C(═O)O—$R_{11}Ar_1$;

$R_{11}$ is C1-C20 alkylene;

$Ar_1$ is C6-C30 aryl;

x is an integer of 10 to 400; and y is an integer of 10 to 100.

In the separation in the step b), an ultrafiltration membrane having a molecular weight cutoff (MWCO) of 3 to 30 kDa may be used.

The steps a) and b) may be performed in a basic solution, and the step c) may be performed in an acidic solution.

The sample containing the glycoproteins may be cells, a cell culture medium, blood, serum, plasma, saliva, urine, cerebrospinal fluid, follicular fluid, breast milk, lens fluid, pancreatic juice, or hydrolyzed polypeptides thereof, the hydrolysis may be performed using an enzyme, and an average molecular weight of the glycoproteins may be 1 to 200 kDa.

Binding and dissociation between aminobenzoboroxole and cis-diols of the glycoproteins according to pH may be used.

Other features and aspects will be apparent from the following detailed description, the drawings, and the claims.

DETAILED DESCRIPTION OF EMBODIMENTS

Figure 1:
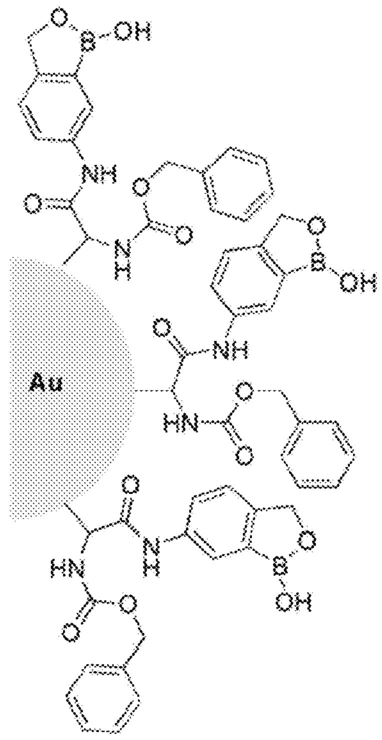
FIG. 1 is a schematic diagram showing a gold nanocluster.

Hereinafter, gold nanoclusters of the present invention, a method of preparing the same, a dopamine biosensor including the same, a method of quantifying dopamine using the same, and a method of diagnosing a neurological disease using the same will be described in detail. In addition, a method of concentrating glycoproteins using the gold nanoclusters, and a method of analyzing disease-specific glycoproteins which includes the method of concentrating glycoproteins using the gold nanoclusters will be described in detail.

Unless the context clearly indicates otherwise, singular forms used in the present invention may be intended to include plural forms.

In addition, a numerical range used in the present invention includes upper and lower limits and all values within these limits, increments logically derived from a form and span of a defined range, all double limited values, and all possible combinations of the upper and lower limits in the numerical range defined in different forms. Unless otherwise specifically defined in the specification of the present invention, values out of the numerical range that may occur due to experimental errors or rounded values also fall within the defined numerical range.

The expression "comprise(s)" described in the present invention is intended to be an open-ended transitional phrase having an equivalent meaning to "include(s)", "contain(s)", "have (has)", and "are (is) characterized by", and does not exclude elements, materials, or steps, all of which are not further recited herein.

The term "aryl" described in the present invention refers to a carbocyclic aromatic group containing 5 to 10 ring atoms. Representative examples thereof include, but are not limited to, phenyl, tolyl, xylyl, naphthyl, tetrahydronaphthyl, anthracenyl, fluorenyl, indenyl, and azulenyl. Furthermore, aryl includes carbocyclic aromatic groups linked by alkylene or alkenylene or linked by one or more heteroatoms selected from B, O, N, C(═O), P, P(═O), S, $S(═O)_2$, and Si atoms.

The term "alkyl" described in the present invention may include both a linear chain form and a branched chain form, and may have 1 to 10 carbon atoms, and preferably 1 to 6 carbon atoms. In addition, in another aspect, the alkyl may have 1 to 3 carbon atoms and preferably 1 or 2 carbon atoms.

The term "alkylene" described in the present invention refers to a divalent organic radical derived by removing one hydrogen from "alkyl", where the alkyl follows the definition of the alkyl above.

The term "diagnosis" described in the present invention refers to confirming the presence or features of pathological conditions.

The term "biomarker" described in the present invention is a substance that may be diagnosed by comparing a diseased group and a control group (normal group), and refers to organic biomolecules which increase in the diseased group compared to the control group (normal group). Examples of the organic biomolecules include polypeptides, proteins, nucleic acids, lipids, glycolipids, glycoproteins, and sugars.

Hereinafter, the present invention will be described in detail. However, unless otherwise defined, all the technical terms and scientific terms used herein have the same meanings as commonly understood by those skilled in the art to which the present invention pertains, and descriptions for the known function and configuration unnecessarily obscuring the gist of the present invention will be omitted in the following descriptions.

The present invention provides gold nanoclusters represented by the following Chemical Formula 1:

[Chemical Formula 1]

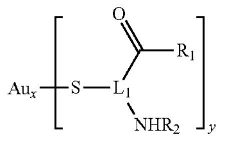

wherein $L_1$ is a trivalent linking group;

the trivalent linking group includes one or two or more linking groups selected from —O—, —C(═O)—, —C(═O)O—, —NH—, and —C(═O)NH—;

$R_1$ is —OH or

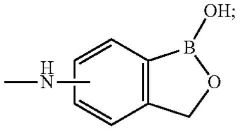

at least one $R_1$ in units y is

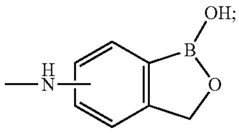

$R_2$ is hydrogen or —C(═O)O—$R_{11}Ar_1$;
at least one $R_2$ in the units y is —C(═O)O—$R_{11}Ar_1$;
$R_{11}$ is C1-C20 alkylene;
$Ar_1$ is C6-C30 aryl;
x is an integer of 10 to 400; and
y is an integer of 10 to 100.
$L_1$ may be substituted with one or two or more substituents selected from —OH, —COOH, and —$NH_2$.

In addition, $L_1$ may be a trivalent linking group represented by the following Chemical Formula 2 or 3:

[Chemical Formula 2]

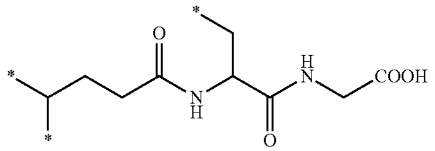

[Chemical Formula 3]

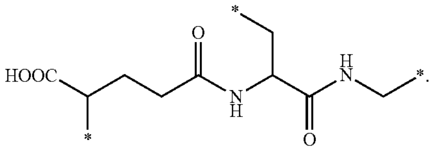

In an exemplary embodiment of the present invention, in Chemical Formula 1, $R_{11}$ may be C1-C5 alkylene, and $Ar_1$ may be C6-C20 aryl, specifically, in Chemical Formula 1, $R_{11}$ may be C1-C3 alkylene, and $Ar_1$ may be C6-C12 aryl, and more specifically, in Chemical Formula 1, $R_{11}$ may be C1-C2 alkylene, and $Ar_1$ may be C6-C10 aryl or phenyl.

In an exemplary embodiment of the present invention, the number of ligands that can bind to the gold nanocluster depends on the number of gold atoms, and specifically, in Chemical Formula 1, x may be 18, 22, 25, 38, 67, 102, 144, or 333, and y may be 14, 18, 24, 35, 44, 60, or 79. For example, when x and y are expressed as (x, y), gold nanoclusters satisfying (18, 14), (22, 18), (25, 18), (38, 24), (67, 35), (102,44), (144,60), or (333,79) may be prepared, in order to precisely control the number of terminal bonds, it is preferable that x is 18, 22, or 25 and y may be 14 or 18, and for example, when x and y are expressed as (x, y), (18,14), (22,18), or (25,18) may be satisfied, but the present invention is not limited thereto.

In addition, according to an exemplary embodiment of the present invention, in Chemical Formula 1, $R_2$ may be each independently hydrogen or

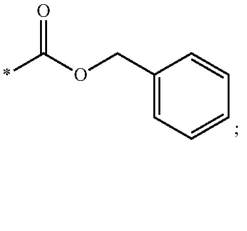 [SMILES: *C(=O)OCc1ccccc1]

and at least one $R_2$ in the units y may be

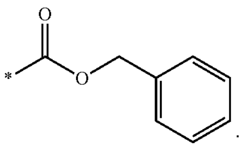 [SMILES: *C(=O)OCc1ccccc1]

As the gold nanoclusters according to the present invention have the configuration described above, solubility thereof in water increases, such that stability may be improved and biocompatibility may be excellent. In addition, amine groups of the gold nanoclusters of the present invention are protected by $R_2$ of Chemical Formula 1, such that the gold nanoclusters are more structurally rigid, and thus the stability of the gold nanoclusters may be increased.

In an exemplary embodiment of the present invention, an average size of the gold nanoclusters may be 10 nm or less, preferably 0.1 to 5 nm, and more preferably 0.5 to 3 nm, but is not limited thereto.

The gold nanoclusters according to the present invention have the configuration described above, such that the gold nanoclusters may implement significantly excellent fluorescence, and may implement a maximized fluorescence effect even in a small amount.

The gold nanoclusters according to an exemplary embodiment may be protected with glutathione as a surface ligand to improve stability and biocompatibility, and may be structurally rigid by introducing benzyl chloroformate (CBz), such that fluorescence intensity and stability of the gold nanoclusters may be increased. In addition, aminobenzoboroxole is introduced, such that the fluorescence intensity and stability may be increased, and it is possible to quantitatively analyze dopamine through a change in fluorescence intensity due to a boronate ester complex, which is a product of the cis-diol reaction between aminobenzoboroxole and dopamine.

Unlike quantum dots, organic nanoparticles, and gold nanoparticles, which are used in dopamine analysis methods using fluorescence in the related art, the gold nanoclusters according to an exemplary embodiment are atomically clearly defined and exhibit more accurate and reproducible fluorescence intensity, such that excellent performance in quantitative analysis of dopamine may be exhibited. In addition, the gold nanoclusters according to an exemplary embodiment exhibit significantly improved fluorescence intensity compared to substances used in the analysis methods according to the related art, and their response to dopamine in a wide concentration range is linear, and therefore, reliability may be shown in a significantly wide detection range.

Regarding the problem of significantly low sensitivity and selectivity of dopamine analysis due to the interference from uric acid, ascorbic acid, and the like in the dopamine analysis methods according to the related art, the gold nanoclusters according to an exemplary embodiment of the present invention exhibit excellent selectivity for dopamine, and thus may exhibit more accurate and highly sensitive dopamine quantitative analysis performance.

The present invention provides a method of preparing gold nanoclusters of the present invention. According to an exemplary embodiment, the method of preparing gold nanoclusters may include: preparing a compound represented by the following Chemical Formula 13 by reacting a compound represented by the following Chemical Formula 11 with a compound represented by the following Chemical Formula 12; and preparing a compound represented by the following Chemical Formula 1 by reacting the compound represented by the following Chemical Formula 13 with a compound represented by the following Chemical Formula 14:

[Chemical Formula 1]

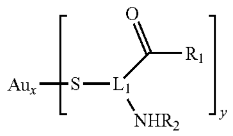

[Chemical Formula 11]

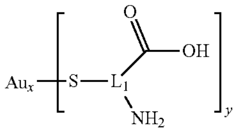

[Chemical Formula 12]

$X'—R_2$

[Chemical Formula 13]

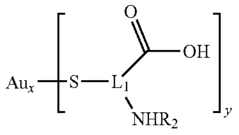

[Chemical Formula 14]

$H—R_1$ wherein $L_1$ is a trivalent linking group;

the trivalent linking group includes one or two or more linking groups selected from —O—, —C(=O)—, —C(=O)O—, —NH—, and —C(=O)NH—;

$R_1$ is

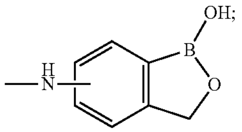

$R_2$ is $—C(=O)O—R_{11}Ar_1$;

$R_{11}$ is C1-C20 alkylene;

$Ar_1$ is C6-C30 aryl;

x is an integer of 10 to 400;

y is an integer of 10 to 100; and

X' is —F, —Cl, —Br, or —I.

$L_1$ may be substituted with one or two or more substituents selected from —OH, —COOH, and $—NH_2$.

The method of preparing gold nanoclusters according to the present invention has excellent reaction activity and stability, such that the number of terminal group bonds may be easily controlled, and gold nanoclusters may be obtained with excellent yield.

The method of preparing gold nanoclusters according to an exemplary embodiment of the present invention may further include a desalination process and a polyacrylamide gel electrophoresis (PAGE) process. Specifically, the desalination process is a process using a dialysis membrane or a filtration membrane, and through this process, $X'—R_2$ and $H—R_1$, which are unreacted by-products, may be removed, and gold nanoclusters into which a certain amount of terminal functional groups are introduced may be separated through the electrophoresis process.

A molar ratio of the compound represented by Chemical Formula 13 to the compound represented by Chemical Formula 14 may be 1:30 to 240, preferably 1:60 to 180, and more preferably 1:70 to 150.

In the method of preparing gold nanoclusters according to an exemplary embodiment of the present invention, the measured value of quantitative analysis of dopamine may be adjusted by adjusting the amount of aminobenzoboroxole introduced into the gold nanoclusters. In the method of preparing gold nanoclusters, the amount of aminobenzoboroxole added may be appropriately adjusted, or the target amount of aminobenzoboroxole introduced may be constantly adjusted through the electrophoresis process.

The method of preparing gold nanoclusters may be performed in an organic solvent. In the case of gold nanoclusters according to the related art, since the reaction was performed under conditions that water was necessarily included, the yield was significantly low due to significantly low reaction activity and stability, and it was difficult to control the number of reaction bonds. In contrast, in the method of preparing gold nanoclusters according to the present invention, the stability of the intermediate may be improved and the reactivity may be increased by using an organic solvent in the reaction step of binding the compounds of Chemical Formulas 12 and 14 to the terminal group of the ligand. Accordingly, the number of bonds of the introduced compounds may be precisely controlled as desired, and the effect of improving fluorescence intensity and dopamine sensitivity may be exhibited by introducing a larger amount of aminobenzoboroxole. The organic solvent used in this case may be any organic solvent that may be recognized by those skilled in the art, specifically, may be one or two or more selected from ethanol, methanol, isopropanol, butanol, pentanol, hexanol, dimethylsulfoxide, dimethylformamide, acetone, acetonitrile, and tetrahydrofuran, and more specifically, may be one or two or more selected from acetone, acetonitrile, and tetrahydrofuran, but is not limited thereto.

In an exemplary embodiment of the present invention, in the step of reacting the compound represented by Chemical Formula 14, a coupling reagent, for example, DCC/NHS coupling reaction, may induce a binding reaction between the carboxyl group of the compound represented by Chemical Formula 13 and the amino group of the compound represented by Chemical Formula 14. Specifically, when the compound represented by Chemical Formula 13 is treated with dicyclohexylcarbodiimide (DCC) to form an unstable ester intermediate and then N-hydroxysuccinimide (NHS) is added, the carboxyl group may be converted to a metastable amine-reactive NHS ester intermediate. The amine-reactive NHS ester intermediate reacts with the amino group of the compound represented by Chemical Formula 14 to form an amide bond. According to an exemplary embodiment of the present invention, a leaving group is a compound fragment that departs with a pair of electrons when heterolysis of a compound occurs in a chemical reaction, and is an anion or a neutral molecule. It is important for the leaving group to have an ability to stabilize an additional pair of electrons departing with the leaving group for separation from the original molecule. According to an exemplary embodiment of the present invention, any leaving group may be used as long as it is a functional group that may be recognized by those skilled in the art, and for example, the leaving group may be a halogen group, an N-succinyl imide group, or the like.

In an exemplary embodiment of the present invention, dicyclohexylcarbodiimide and N-hydroxysuccinimide may be contained at a molar ratio of 1:0.1 to 5, and preferably, may be contained at a molar ratio of 1:1 to 4 for smooth binding, but are not limited thereto.

The present invention provides a dopamine biosensor including the gold nanoclusters according to an exemplary embodiment, and the dopamine biosensor may detect dopamine through a change in fluorescence intensity of the gold nanoclusters due to binding of aminobenzoboroxole to dopamine.

The present invention provides a method of quantifying dopamine, and the method of quantifying dopamine according to an exemplary embodiment may include: preparing a sample containing dopamine; culturing the sample with a sensing solution containing the gold nanoclusters of the present invention; measuring fluorescence intensity by irradiating the cultured sensing solution with light; and quantifying dopamine in the sample by comparing the fluorescence intensity with a calibration curve.

The sensing solution may contain a PBS buffer and gold nanoclusters, and a concentration of the gold nanoclusters contained in the PBS buffer may be 0.1 to 1.5 mg/mL, specifically, 0.3 to 1.2 mg/mL, and more specifically, 0.5 to 1.0 mg/mL, but is not limited thereto.

In addition, in the culturing of the sample containing dopamine and the sensing solution, a volume ratio of the sample containing dopamine to the sensing solution may be 1:100 to 1,000, specifically, 1:150 to 700, and more specifically, 1:200 to 400, but is not limited thereto.

Examples of techniques used for quantitative analysis of dopamine include immunoassay, spectrophotometry, chromatography, and electrochemical methods. Chromatography has limited spectral resolution and is significant time consuming, and electrochemical methods are interfered with analytes having similar redox potentials. The analysis method using fluorescence used in the method of quantifying dopamine in the present invention has the advantages of excellent reproducibility and sensitivity, quick and easy workability, easy visualization of results, and low cost compared to other analysis methods.

In the quantitative analysis of dopamine according to an exemplary embodiment of the present invention, a wavelength of the irradiated light may be 520 nm, and a wavelength of the fluorescence to be measured may be 640 nm. The gold nanoclusters of the present invention emit fluorescence with a wavelength of 640 nm when irradiated with light with a wavelength of 520 nm, and the fluorescence may be used for quantitative analysis of dopamine by analyzing a variation in fluorescence with a wavelength of 640 nm, which decreases when the sensing solution containing the gold nanoclusters binds to dopamine. The gold nanoclusters according to the present invention show a significantly constant variation in fluorescence in a wider range of dopamine concentrations ranging from 0 to 100 μM, and thus may be used as an excellent dopamine sensor with a significantly wide detection range.

In addition, the present invention provides a method of diagnosing a neurological disease, and the method of diagnosing a neurological disease according to an exemplary embodiment may include: separating serum from a collected blood sample; mixing the gold nanoclusters of the present invention with the separated serum to obtain a mixed solution and culturing the mixed solution; measuring fluorescence intensity by irradiating the cultured solution with light; and quantifying dopamine in the blood sample by comparing the fluorescence intensity with a calibration curve.

The separated serum may be diluted 10 to 500-fold, specifically, 30 to 400-fold, and more specifically, 50 to 300-fold, but is not limited thereto.

In addition, a concentration of the gold nanoclusters mixed with the serum may be 0.1 to 1.5 mg/mL, specifically, 0.3 to 1.2 mg/mL, and more specifically, 0.5 to 1.0 mg/mL, but is not limited thereto.

The neurological disease may be one or two or more selected from a motor disorder, depression, an emotional disturbance, obsessive-compulsive disorder, autism, schizophrenia, attention deficit hyperactivity disorder, Alzheimer's disease, Parkinson's disease, Creutzfeldt-Jakob disease, dementia, and Huntington's disease.

In addition, the present invention provides a method of concentrating glycoproteins using the gold nanoclusters according to an exemplary embodiment.

Specifically, the method of concentrating glycoproteins according to the present invention may include: a) mixing gold nanoclusters represented by the following Chemical Formula 1 with a sample containing glycoproteins; b) separating the gold nanoclusters complexed with the glycoproteins; and c) separating the glycoproteins and the gold nanoclusters:

[Chemical Formula 1]

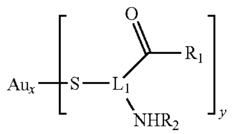

wherein $L_1$ is a trivalent linking group;

the trivalent linking group includes one or two or more linking groups selected from —O—, —C(═O)—, —C(═O)O—, —NH—, and —C(═O)NH—;

each $R_1$ is independently —OH or

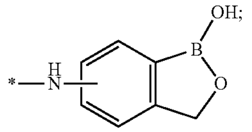

at least one $R_1$ in units y is

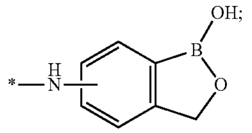

each $R_2$ is independently hydrogen or —C(═O)O—$R_{11}Ar_1$;

at least one $R_2$ in the units y is —C(═O)O—$R_{11}Ar_1$;

$R_{11}$ is C1-C20 alkylene;

$Ar_1$ is C6-C30 aryl;

x is an integer of 10 to 400; and y is an integer of 10 to 100.

The boronic acid-functionalized gold nanoclusters according to the present invention have an atomically defined surface structure, and a chemical structure and number of surface functional groups may be precisely controlled. Therefore, non-specific binding to glycoproteins may be remarkably lowered.

A particle size of the gold nanoclusters represented by Chemical Formula 1 of the present invention may be 1 to 10 nm, specifically, 1 to 5 nm, and more specifically, 1 to 3 nm. As described above, the gold nanoclusters of the present invention exhibit a smaller particle size than other solid phases used for glycoprotein concentration in the related art, such that the gold nanoclusters have improved solubility and have a large surface area, thereby exhibiting excellent concentration efficiency.

In the method of concentrating glycoproteins according to an exemplary embodiment of the present invention, binding and dissociation between aminobenzoboroxole and cis-diols of the glycoproteins according to pH may be used.

The binding of aminobenzoboroxole to cis-diols of the glycoproteins may be specific, and the structure of the sugar or sugar chain is maintained even after the binding and dissociation, such that diagnosis of a disease exhibiting a specific sugar or sugar chain may be facilitated.

According to an exemplary embodiment of the present invention, a concentration of the gold nanoclusters in the step a) may be 1 to 15 mg/mL, specifically, 3 to 12 mg/mL, and more specifically, 5 to 10 mg/mL, but is not limited thereto.

According to an exemplary embodiment of the present invention, in the separation in the step b), an ultrafiltration membrane having a molecular weight cutoff (MWCO) of 3 to 30 kDa may be used, specifically, an ultrafiltration membrane having a molecular weight cutoff (MWCO) of 5 to 17 kDa may be used, and more specifically, an ultrafiltration membrane having a molecular weight cutoff (MWCO) of 7 to 15 kDa may be used, but the present invention is not limited thereto.

In the method of concentrating glycoproteins according to an exemplary embodiment, the steps a) and b) may be performed in a basic solution, specifically, may be performed in a solution with a pH of 7.5 to 10.5, and more specifically, may be performed in a solution with a pH of 7 to 10.

In addition, the step c) may be performed in an acidic solution, specifically, may be performed in a solution with a pH of 1 to 4, and more specifically, may be performed in a solution with a pH of 2 to 3.

The method of concentrating glycoproteins according to an exemplary embodiment of the present invention may further include, after the step c), additionally adding an acidic solution, and specifically, the acidic solution may be formic acid or acetic acid. As such, when the acidic solution is slowly added, the gold nanoclusters according to an exemplary embodiment are precipitated, and dissolved concentrated glycoproteins may be separated from the precipitated gold nanoclusters.

The binding and dissociation of the boronic acid-functionalized gold nanoclusters according to the present invention may be easily performed only by adjusting pH using binding of aminobenzoboroxole to a cis-diol of a sugar or sugar chain, and the dissociated boronic acid-functionalized gold nanoclusters may be reused, which may be significantly cost-effective.

According to an exemplary embodiment of the present invention, the sample containing glycoproteins may be cells, a cell culture medium, blood, serum, plasma, saliva, urine, cerebrospinal fluid, follicular fluid, breast milk, lens fluid, pancreatic juice, or hydrolyzed polypeptides thereof, and the hydrolysis may be performed using an enzyme.

Specifically, the enzyme may be one or two or more selected from arginine C (Arg-C), aspartic acid N (Asp-N), glutamic acid C (Glu-C), lysine C (Lys-C), chymotrypsin, and trypsin, but is not limited thereto.

In addition, an average molecular weight of the glycoproteins used in the method of concentrating glycoproteins according to an exemplary embodiment of the present invention may be 1 to 200 kDa, specifically, 5 to 150 kDa, and more specifically, 10 to 100 kDa, but is not limited thereto.

The present invention provides a method of analyzing disease-specific glycoproteins, the method including: performing mass spectrometry on glycoproteins concentrated by the method of concentrating glycoproteins according to an exemplary embodiment of the present invention; and screening peptides showing a significant change in amount compared to that of a control group.

In the method of analyzing disease-specific glycoproteins, mass spectrometry may be performed on the concentrated glycoproteins without a pretreatment, or mass spectrometry may be performed on the concentrated glycoproteins after performing hydrolysis using an enzyme. The enzyme may be one or two or more selected from arginine C (Arg-C), aspartic acid N (Asp-N), glutamic acid C (Glu-C), lysine C (Lys-C), chymotrypsin, and trypsin, but is not limited thereto.

Through the mass spectrometry of the concentrated glycoproteins, peptide sequencing of the concentrated glycoproteins is possible, such that it is possible to discover glycoproteomics-based biomarkers by comparatively analyzing the sequencing of the control group and the diseased group. From this, it is possible to efficiently diagnose a specific disease by tracking a quantitative change of a specific sugar or glycosylated glycoprotein according to the occurrence of a specific disease.

Hereinafter, the gold nanoclusters according to the present invention, the method of preparing the same, the dopamine biosensor including the same, the method of quantifying dopamine using the same, and the method of diagnosing a neurological disease using the same will be described in more detail with reference to specific Examples. In addition, the method of concentrating glycoproteins using the gold nanoclusters according to the present invention and the method of analyzing disease-specific glycoproteins which includes the method of concentrating glycoproteins using the gold nanoclusters will be described in more detail.

However, the following Examples are only reference examples for describing the present invention in detail, and the present invention is not limited thereto and may be implemented in various forms. In addition, the terms used in the present invention are only to effectively describe specific Examples, but are not intended to limit the present invention.

[Example 1] Preparation of $Au_{22}$—CBz-BX 0.25 mmol of $HAuCl_4 \cdot 3H_2O$ dissolved in 12.50 mL of water and 0.37 mmol of glutathione (GS) dissolved in 7.50 mL of water were simultaneously added to 230 mL of water, stirring was performed for 2 minutes, and then, when the color of the solution was changed to turbid yellow, 1 M NaOH was added to increase the pH to 12. 0.1 mL of 3.5 mM $NaBH_4$ was slowly added dropwise to the solution. Thereafter, the mixed solution was stirred for 30 minutes, the pH of the solution was lowered to 2.5 using 1 M HCl, and then stirring was performed at room temperature for 6 hours. When the reaction was completed, the solvent was completely removed by rotary evaporation, and then a recrystallization process of precipitating a solid using a centrifuge was performed, the solid being formed by dissolving the resultant in 10 mL of water and adding 12 mL of isopropanol, thereby obtaining $Au_{22}GS_{18}$ nanoclusters.

10 mg of the prepared $Au_{22}GS_{18}$ nanoclusters were dissolved in 1 mL of distilled water contained in a 20 mL vial, and then 1 mg of $NaHCO_3$ was added. A solution obtained by dissolving 20 μL of benzyl chloroformate (CBz) in 1 mL of tetrahydrofuran (THF) was added, and stirring was performed for 3 hours. The addition ratio was $CBz/Au_{22}$=270, which means the addition with a composition ratio of CBz 10 times per GS. Thereafter, unreacted benzyl chloroformate (CBz) was removed through a desalting column with 3 kDa to obtain $Au_{22}$—$CBz_{18}$ nanoclusters.

10 mg of the prepared $Au_{22}$—$CBz_{18}$ nanoclusters were dissolved in 1 mL of 25 mM phosphate buffered saline (PBS) contained in a 20 mL vial, and then 21 mg of N-hydroxysuccinimide (NHS) was added. A solution obtained by dissolving 30.2 mg of dicyclohexylcarbodiimide (DCC) in 2 mL of tetrahydrofuran (THF) was added, and stirring was performed for 30 minutes. A solution obtained by dissolving 33.9 mg of 5-aminobenzoboroxole (BX) in 3 mL of tetrahydrofuran (THF) was added, 0.3 mL of water was added, and stirring was performed for 24 hours. Thereafter, unreacted 5-aminobenzoboroxole (BX) was removed through a desalting column with 10 kDa, polyacrylamide gel electrophoresis (PAGE) was performed at 150 V for 2 hours or longer, thereby obtaining $Au_{22}$—$CBz_{18}$-$BX_{24}$ nanoclusters.

Figure 2:
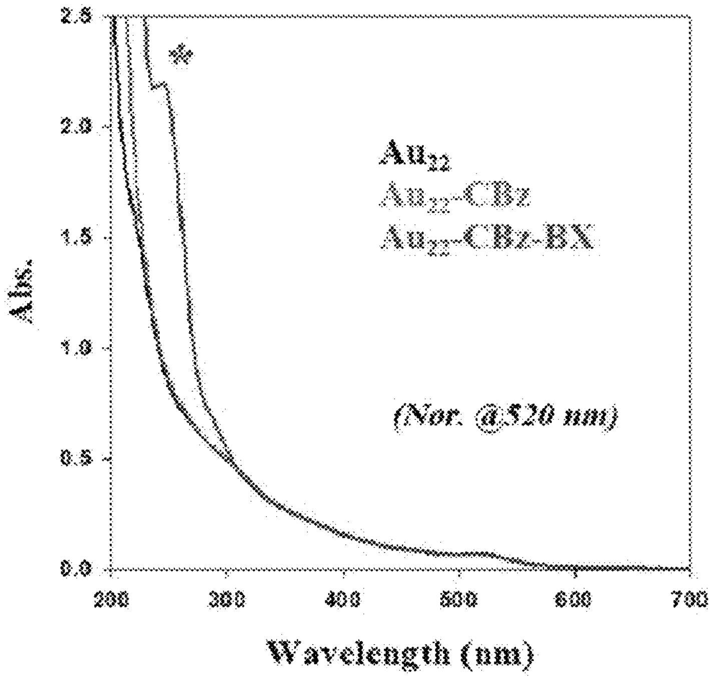
FIG. 2 is a diagram showing an absorption spectrum in Example 1.
Figure 3:
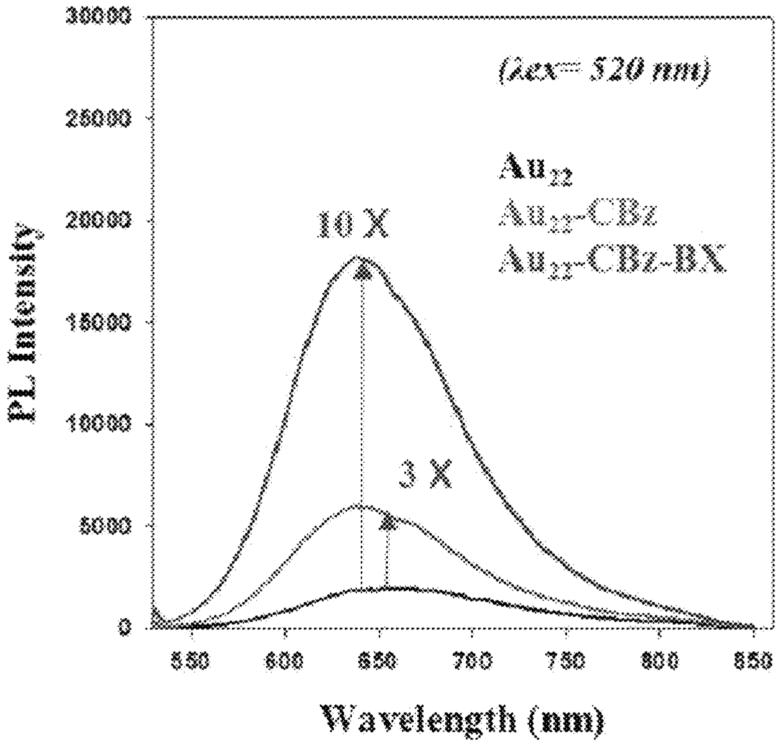
FIG. 3 is a diagram showing a fluorescence spectrum in Example 1.

The absorption spectrum of the prepared $Au_{22}$—$CBz_{18}$-$BX_{24}$ nanoclusters is shown in FIG. 2. It could be seen that the characteristic absorption peak of BX appeared at 200 to 300 nm. The fluorescence spectrum of the prepared $Au_{22}$—$CBz_{18}$-$BX_{24}$ nanoclusters is shown in FIG. 3. It could be seen that the fluorescence was improved to 10 times by introducing CBz and BX into the gold nanoclusters.

Figure 4:
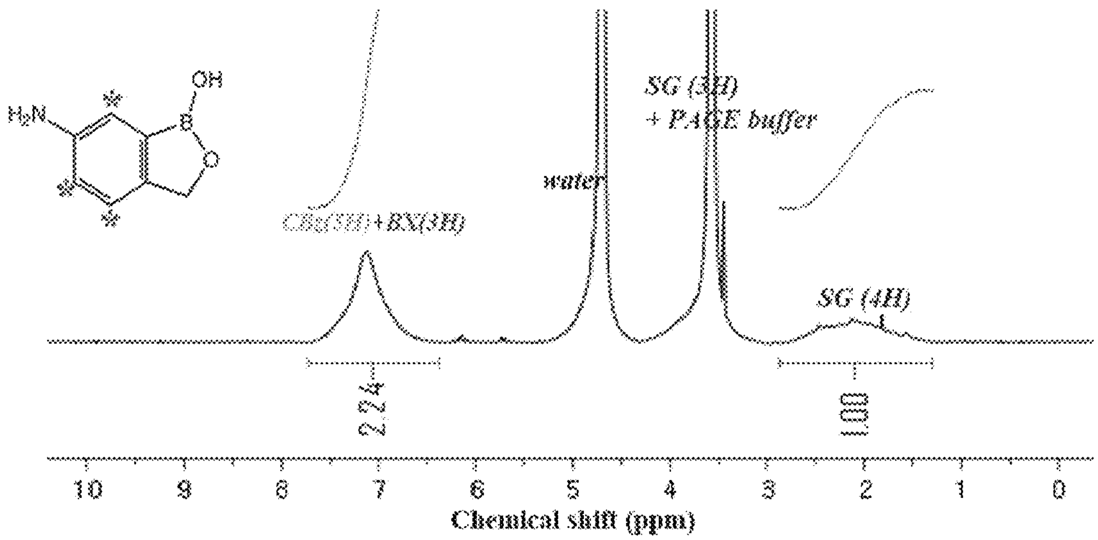
FIG. 4 is a diagram showing 1H NMR in Example 1.

In addition, 1H NMR of the prepared $Au_{22}$—$CBz_{18}$-$BX_{24}$ nanoclusters is shown in FIG. 4. It could be seen that 23.8 BXs were introduced by comparing eight hydrogen peaks of CBz and BX and four hydrogen peaks of glutathione.

[Comparative Example 1] Preparation of Gold Nanoclusters 0.25 mmol of $HAuCl_4 \cdot 3H_2O$ dissolved in 12.50 mL of water and 0.37 mmol of glutathione (GS) dissolved in 7.50 mL of water were simultaneously added to 230 mL of water, the mixed solution was stirred for 2 minutes, and then, when the color of the solution was changed to turbid yellow, 1 M NaOH was added to increase the pH to 12. 0.1 mL of 3.5 mM $NaBH_4$ was slowly added dropwise to the solution. Thereafter, the mixed solution was stirred for 30 minutes, the pH of the solution was lowered to 2.5 using 1 M HCl, and then stirring was performed at room temperature for 6 hours. When the reaction was completed, the solvent was completely removed by rotary evaporation, and then a recrystallization process of precipitating a solid using a centrifuge was performed, the solid being formed by dissolving the resultant in 10 mL of water and adding 12 mL of isopropanol, thereby obtaining $Au_{22}GS_{18}$ nanoclusters.

10 mg of the prepared $Au_{22}GS_{18}$ nanoclusters were dissolved in 1 mL of distilled water contained in a 20 mL vial, and then 1 mg of $NaHCO_3$ was added. A solution obtained by dissolving 20 μL of benzyl chloroformate (CBz) in 1 mL of tetrahydrofuran (THF) was added, and stirring was performed for 3 hours. The addition ratio was $CBz/Au_{22}$=270, which means the addition with a composition ratio of CBz 10 times per GS. Thereafter, unreacted benzyl chloroformate (CBz) was removed through a desalting column with 3 kDa to obtain $Au_{22}$—$CBz_{18}$ nanoclusters.

Experimental Example 1

Figure 5:
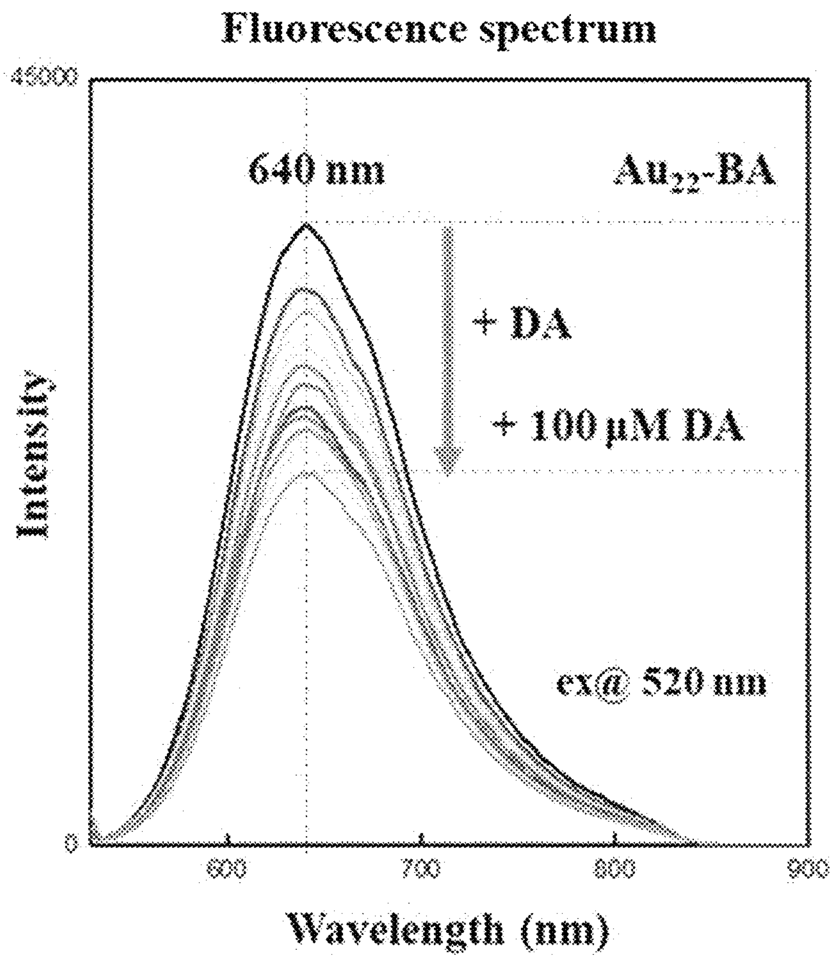
FIG. 5 is a diagram showing a fluorescence spectrum according to a change in concentration of dopamine in Experimental Example 1.
Figure 6:
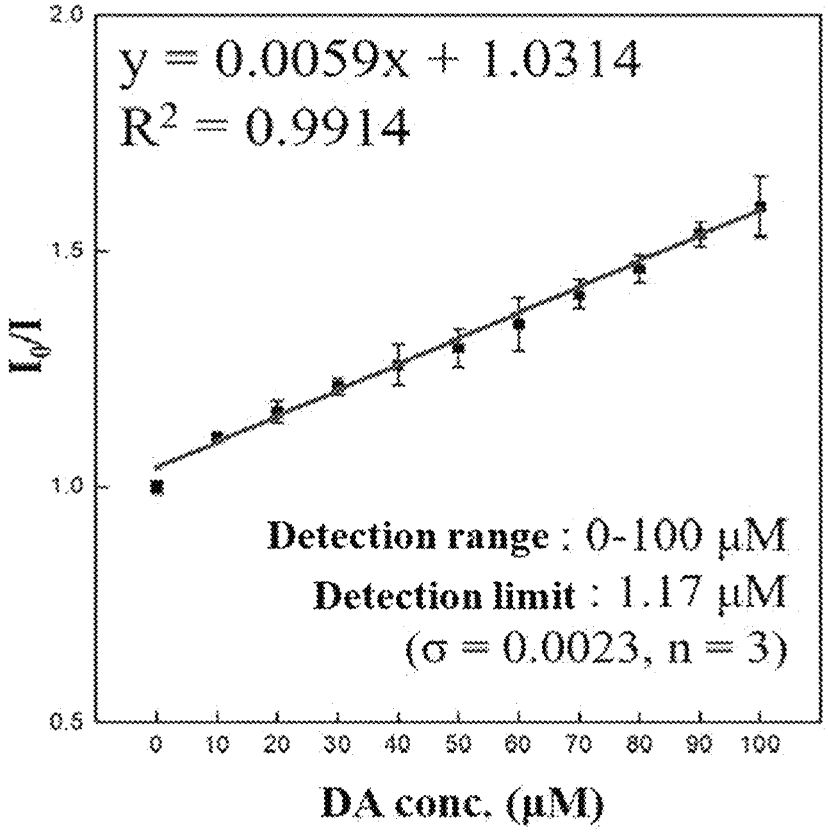
FIG. 6 is a diagram showing a variation in fluorescence according to the change in concentration of dopamine in Experimental Example 1.

To 3 mL of 0.1 M PBS buffer (pH=9) in which 2 mg of the gold nanoclusters of Example 1 were dissolved, 0 to 0.01 mL of a 30 mM dopamine aqueous solution was added so that a final concentration of dopamine was 0 to 100 μM, the mixed solution was incubated at room temperature for 5 minutes, and then a fluorescence spectrum was analyzed. The analyzed fluorescence spectrum is shown in FIG. 5. It could be confirmed that the fluorescence intensity at 640 nm constantly decreased as the concentration of dopamine increased. Based on these results, a graph of the relationship between the concentration of dopamine and the change in fluorescence intensity is shown in FIG. 6. It could be confirmed that the change in fluorescence intensity occurred linearly as the concentration of dopamine increased. That is, a linear result of $R^2$ of 0.9914 was obtained in a wide concentration range of 0 to 100 μM. Therefore, it can be appreciated that the dopamine biosensor including the gold nanoclusters of Example 1 of the present invention has a significantly wide detection range.

Experimental Example 2

The selectivity for ascorbic acid, uric acid, and various amino acids that may interfere with the quantitative analysis of dopamine was analyzed.

Figure 7:
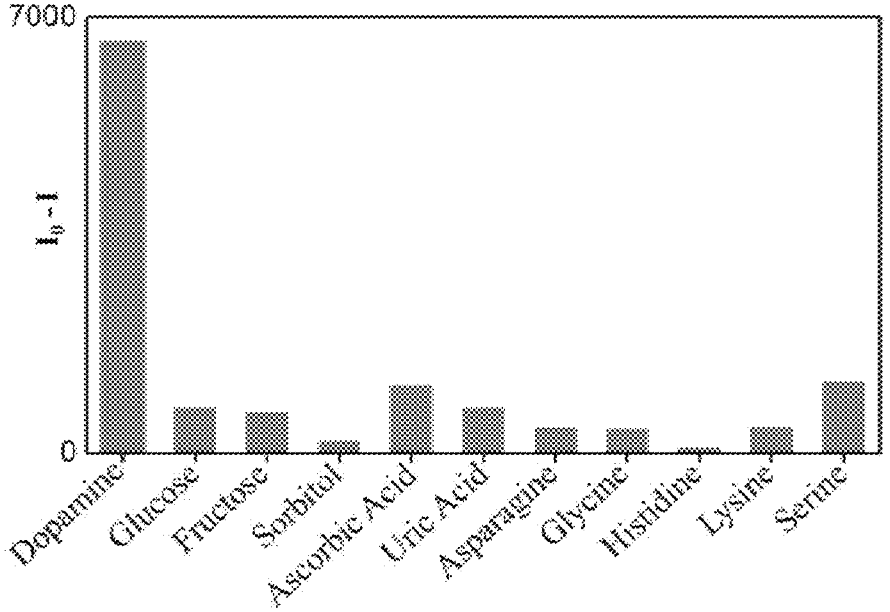
FIG. 7 is a graph showing selectivity for dopamine in Experimental Example 2.

30 mM aqueous sample solutions were prepared so that the concentrations of dopamine, ascorbic acid, uric acid, glucose, fructose, sorbitol, asparagine, glycine, histidine, lysine, and serine were each at a concentration of 100 μM in the final solution, 0.01 mL of each of the aqueous sample solutions was added to 3 mL of a 0.1 M PBS buffer (pH=9) in which 2 mg of the gold nanoclusters of Example 1 were dissolved, the mixed solution was incubated at room temperature for 5 minutes, and then the fluorescence spectrum was analyzed. The results are shown in FIG. 7. As shown in FIG. 7, it can be appreciated that the dopamine biosensor including the gold nanoclusters of Example 1 of the present invention exhibits excellent selectivity for dopamine compared to substances that may cause interference.

Experimental Example 3

A spike and recovery experiment was performed to analyze the performance of the dopamine biosensor including the gold nanoclusters of Example 1 of the present invention using a serum sample.

2 mg of the gold nanoclusters of Example 1 were added to 3 mL of a supernatant obtained by diluting a human serum (Sigma-Aldrich) sample 100 times and centrifuging the diluted human serum at 4,000 rpm and room temperature for 10 minutes. 0.0025 mL, 0.0050 mL, and 0.0075 mL of 30 mM dopamine solutions were added so that the final concentrations of dopamine were 25 μM, 50 μM, and 75 μM, respectively, the fluorescence spectrum was measured, and dopamine in the sample was quantified by comparing the measured fluorescence spectrum with the calibration curve of Experimental Example 1. The results are shown in Table 1.

TABLE 1

| Concentration of injected dopamine (μM) | Measured concentration of dopamine (μM) | Recovery (%) | Relative standard deviation (%) (n = 3) |
|---|---|---|---|
| 25 | 28.3 | 113.2 | 2.73 |
| 50 | 45.7 | 91.4 | 2.75 |
| 75 | 68.5 | 91.3 | 3.11 |

As shown in Table 1, all of the recoveries obtained by comparing the concentrations of injected dopamine and the measured concentrations of dopamine showed results of 90 to 115%, and therefore, it could be confirmed that all the dopamine biosensors had excellent accuracy and reproducibility. Therefore, it is expected that the practical potential of the dopamine biosensor of the present invention is significantly high.

From these results, it can be appreciated that the dopamine biosensor including the gold nanoclusters of Example 1 of the present invention may exhibit improved fluorescence intensity, exhibits a wide detection range in quantitative analysis of dopamine, and has excellent selectivity for dopamine. In addition, it can be appreciated that the dopamine biosensor is a highly practical means because it shows an excellent recovery for human serum through the spike and recovery experiment.

Experimental Example 4

0.5 mg of the gold nanoclusters of Example 1 were dissolved in 100 μL of a 0.1 M PBS buffer (pH=9), 1.3 mg of vancomycin, a standard glycopeptide, was added, and the solution was incubated at room temperature for 30 minutes. Thereafter, centrifugation was performed three times at 4,000 rpm for 7 minutes using a 10 k MWCO ultrafiltration membrane to separate the gold nanoclusters complexed with the glycopeptides. The separated gold nanoclusters complexed with the glycopeptides were added to a solution (ACN:DIW:TEA=50:49:1), the glycoproteins and the gold nanoclusters were separated, 0.1% formic acid was added dropwise to precipitate the gold nanoclusters, and then filtration and desalination processes were performed, thereby obtaining concentrated glycopeptides.

Figure 8:
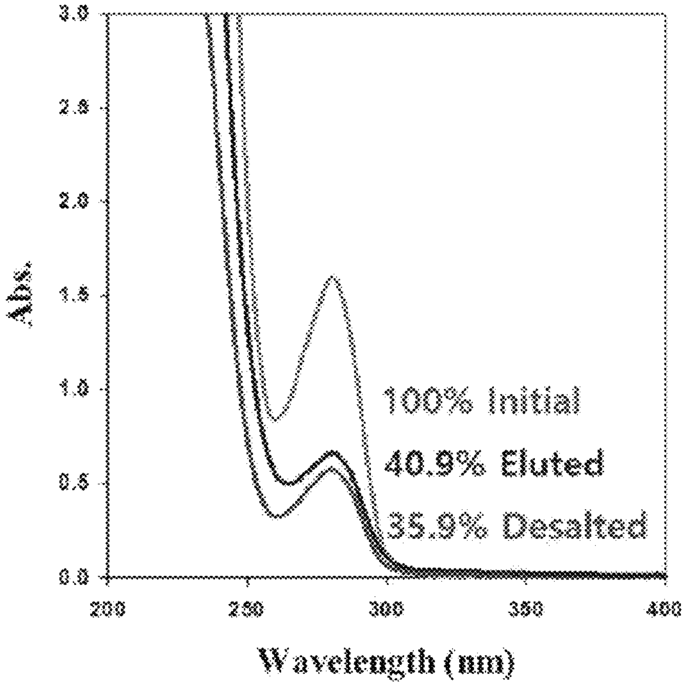
FIG. 8 is a diagram showing results of analysis using a UV-vis NIR spectrophotometer in Experimental Example 4.

The initial glycopeptides and concentrated glycopeptides were analyzed using a UV-vis-NIR spectrophotometer (UV-3600, Shimadzu Corporation). The results are shown in FIG. 8. As shown in FIG. 8, the recovery was 35.9%, from which the effectiveness of the method of concentrating glycoproteins of the present invention could be confirmed.

Experimental Example 5

Figure 9:
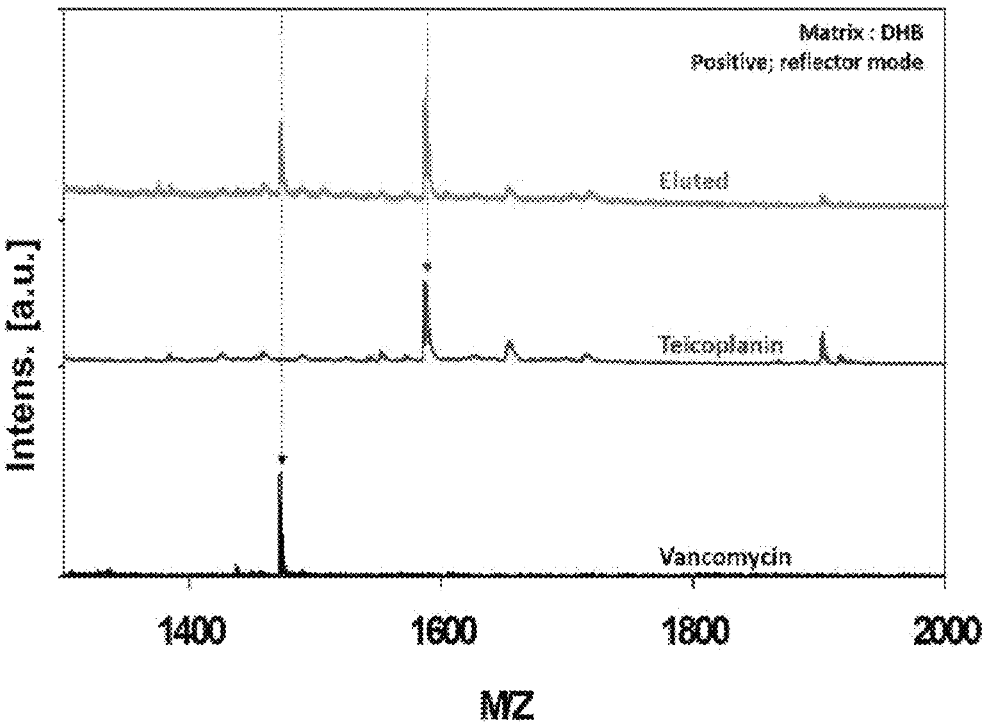
FIG. 9 is a diagram showing results of analysis using a mass spectrometer in Experimental Example 5.

Concentrated glycopeptides were obtained in the same manner as that of Experimental Example 4, except that both vancomycin and teicoplanin were used instead of vancomycin, and then mass spectrometry was performed using a mass spectrometer (MALDI-TOF-MS, Autoflex Max, Bruker Corporation). The results are shown in FIG. 9. Vancomycin and teicoplanin were analyzed as shown in FIG. 9, from which the effectiveness of the method of concentrating glycoproteins of the present invention could be confirmed.

Experimental Example 6

Concentrated glycopeptides were obtained in the same manner as that of Experimental Example 4, except that both the gold nanoclusters of Example 1 and the gold nanoclusters of Comparative Example 1 were used instead of the gold nanoclusters of Example 1, and both vancomycin and teicoplanin were used instead of vancomycin, and then the initial glycopeptides and concentrated glycopeptides were analyzed using a UV-vis-NIR spectrophotometer (UV-3600, Shimadzu Corporation). The results are shown in Table 2.

TABLE 2

| | | Example 1 | Comparative Example 1 |
|---|---|---|---|
| Vancomycin | Recovery (%) | 11.7 | 9.6 |
| | Number of glycopeptides bound per gold nanocluster | 0.23 | 0.19 |
| Teicoplanin | Recovery (%) | 44.9 | 8.2 |
| | Number of glycopeptides bound per gold nanocluster | 0.92 | 0.16 |

As shown in Table 2, it could be appreciated that in Example of the present invention, an excellent recovery was exhibited and thus significantly improved concentration efficiency was exhibited. In addition, in the result of the number of glycopeptides bound per gold nanocluster of Example 1, there was a 4-fold difference between vancomycin having one cis-diol in the compound and teicoplanin having four cis-diols in the compound, and thus, it could be appreciated that the concentration efficiency increased in direct proportion to the number of binding sites of the glycopeptide. Therefore, it can be confirmed that the method of concentrating glycoproteins using the boronic acid-functionalized gold nanoclusters of the present invention exhibits excellent selectivity.

The boronic acid-functionalized gold nanoclusters of the present invention have a small particle size, and thus have excellent solubility, a large surface area, and an excellent binding ability to a cis-diol, thereby exhibiting significantly improved concentration efficiency. The boronic acid-functionalized gold nanoclusters of the present invention have an atomically defined surface structure, such that regular surface functional groups may be controlled to minimize non-specific binding, and the binding and dissociation of the boronic acid-functionalized gold nanoclusters of the present invention may be easily performed without changing the shape or structure of the sugar or sugar chain according to pH, resulting in clearer diagnosis of diseases.

In addition, the boronic acid-functionalized gold nanoclusters of the present invention may be easily separated and reused according to pH, and thus may be used in the method of concentrating glycoproteins that is more economical and exhibits excellent efficiency.

As set forth above, the novel gold nanoclusters of the present invention exhibit excellent fluorescence intensity and may exhibit accurate and reproducible fluorescence intensity because they are atomically clearly defined.

The dopamine biosensor including the gold nanoclusters and the method of quantifying dopamine of the present invention exhibit excellent selectivity for dopamine and a linear response to dopamine in a wide concentration range, such that a wide detection range may be exhibited.

Further, when the dopamine sensor including the gold nanoclusters of the present invention is used, it is possible to diagnose neurological diseases more accurately and reproducibly.

Further, the gold nanoclusters of the present invention have a small particle size, and thus have excellent solubility and a large surface area, thereby exhibiting excellent glycoprotein concentration efficiency. When the gold nanoclusters of the present invention are used, non-specific binding may be minimized compared to the existing methods of concentrating glycoproteins using other solid phases.

Further, the gold nanoclusters of the present invention may control binding and dissociation with cis-diol-containing glycoproteins according to pH conditions, such that the glycoproteins may be concentrated with a simple operation. The gold nanoclusters may be reused and thus may be more cost-effective.

The method of analyzing disease-specific glycoproteins, which includes the method of concentrating glycoproteins using the gold nanoclusters of the present invention, may be easily used for diagnosis of a disease by identifying different glycoprotein peptide sequences, sugar forms, and sugar structures in the patient group compared to the normal group.

Hereinabove, although the present invention has been described by specific matters and limited Examples and Comparative Examples, they have been provided only for assisting in the entire understanding of the present invention. Therefore, the present invention is not limited to the Examples. Various modifications and changes may be made by those skilled in the art to which the present invention pertains from this description.

Therefore, the spirit of the present invention should not be limited to the described exemplary embodiments, but the claims and all modifications equal or equivalent to the claims are intended to fall within the spirit of the present invention.

What is claimed is:

1. Gold nanoclusters represented by the following Chemical Formula 1:

[Chemical Formula 1]

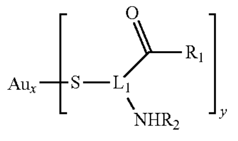

wherein $L_1$ is a trivalent linking group;

the trivalent linking group includes one or two or more linking groups selected from —O—, —C(═O)—, —C(═O)O—, —NH—, and —C(═O)NH—;

$R_1$ is —OH or

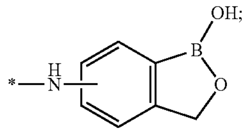

at least one $R_1$ in units y is

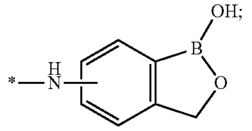

$R_2$ is hydrogen or —C(═O)O—$R_{11}Ar_1$;

at least one $R_2$ in the units y is —C(═O)O—$R_{11}Ar_1$;

$R_{11}$ is C1-C20 alkylene;

$Ar_1$ is C6-C30 aryl;

x is an integer of 10 to 400; and y is an integer of 10 to 100.

2. The gold nanoclusters of claim 1, wherein $L_1$ has one or two or more substituents selected from —OH, —COOH, and —$NH_2$.

3. The gold nanoclusters of claim 1, wherein $L_1$ is a trivalent linking group represented by the following Chemical Formula 2 or 3:

[Chemical Formula 2]

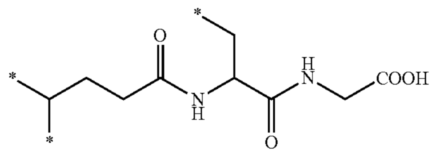

[Chemical Formula 3]

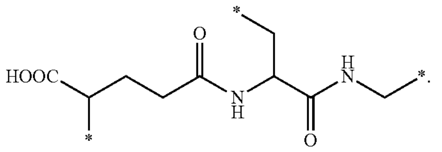

4. The gold nanoclusters of claim 1, wherein in Chemical Formula 1, $R_{11}$ is C1-C5 alkylene, and Aris C6-C20 aryl.

5. The gold nanoclusters of claim 1, wherein in Chemical Formula 1, x is 18, 22, 25, 38, 67, 102, 144, or 333, and y is 14, 18, 24, 35, 44, 60, or 79.

* * * * *